United States Patent
Kawada (10) Patent No.: US 10,048,129 B2
(45) Date of Patent: Aug. 14, 2018

(54) TOTAL REFLECTION SPECTROSCOPIC MEASUREMENT DEVICE AND TOTAL REFLECTION SPECTROSCOPIC MEASUREMENT METHOD

(71) Applicant: HAMAMATSU PHOTONICS K.K., Hamamatsu-shi, Shizuoka (JP)

(72) Inventor: Yoichi Kawada, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/597,329

(22) Filed: May 17, 2017

(65) Prior Publication Data
US 2017/0336259 A1 Nov. 23, 2017

(30) Foreign Application Priority Data

May 20, 2016 (JP) ................................. 2016-101709

(51) Int. Cl.
*G01J 3/14* (2006.01)
*G01J 3/447* (2006.01)
*G01N 21/25* (2006.01)

(52) U.S. Cl.
CPC ................. *G01J 3/14* (2013.01); *G01J 3/447* (2013.01); *G01N 21/255* (2013.01)

(58) Field of Classification Search
CPC ........... G01J 3/14; G01J 3/447; G01N 21/255
See application file for complete search history.

(56) References Cited

U.S. PATENT DOCUMENTS

| | | | | |
|---|---|---|---|---|
| 2003/0016358 A1* | 1/2003 | Nagashima | ............ | G01N 21/21 356/364 |
| 2006/0068513 A1* | 3/2006 | Funakubo | ............... | C23C 16/52 438/14 |
| 2008/0273207 A1* | 11/2008 | Sekiguchi | .......... | G01N 21/3581 356/445 |
| 2016/0069673 A1* | 3/2016 | Takayanagi | ........ | G01B 11/0641 250/339.11 |

OTHER PUBLICATIONS

Hideki Hirori, et al., "Attenuated Total Reflection Spectroscopy in Time Domain Using Terahertz Coherent Pulses," Japanese Journal of Applied Physics, 2004 vol. 43, No. 10A, p. L1287-p. L1289.

* cited by examiner

*Primary Examiner* — Hugh H Maupin
(74) *Attorney, Agent, or Firm* — Drinker Biddle & Reath LLP (57) ABSTRACT

A total reflection spectroscopic measurement device includes a terahertz wave generation unit, an internal total reflection prism, a detection unit configured to detect the terahertz wave, an electric field vector measurement unit configured to measure an electric field vector of the terahertz wave, and an analysis unit configured to acquire information about an optical constant of the object to be measured. Proportions of S polarization component and P polarization component of the terahertz wave are constant. The analysis unit acquires the information about the optical constant on the basis of a ratio between S polarization component and P polarization component of the measured electric field vector when the object is not arranged on the total reflection surface and a ratio between S polarization component and P polarization component of the measured electric field vector when the object is arranged on the total reflection surface.

6 Claims, 6 Drawing Sheets

TOTAL REFLECTION SPECTROSCOPIC MEASUREMENT DEVICE AND TOTAL REFLECTION SPECTROSCOPIC MEASUREMENT METHOD

TECHNICAL FIELD

An aspect of the present invention relates to a total reflection spectroscopic measurement device and a total reflection spectroscopic measurement method.

BACKGROUND

Total reflection spectroscopic measurement for measuring an object to be measured arranged on a total reflection surface of a prism using a terahertz wave is conventionally known. For example, as disclosed in Non-Patent Literature 1 (H. Hirori, K. Yamashita, M. Nagai, and K. Tanaka, "Attenuated total reflection spectroscopy in time domain using terahertz coherent pulses," Jpn. J. Appl. Phys. 43, L1287, (2004)), a signal measured in a state in which the object to be measured is not arranged on the total reflection surface of the prism is used as a reference in conventional total reflection spectroscopic measurement. Then, a signal obtained by measuring the object to be measured is compared with the reference and an optical constant of the object to be measured is derived from a degree of change in the two signals.

SUMMARY

In the conventional technology as described above, a light source like, for example, a femtosecond laser, is used to generate a terahertz wave. Power of such a light source may vary greatly with time. Thus, if a time interval between measurement of the reference and measurement of the object to be measured is long, the power of the light source is considered to have changed during the time interval. In this case, even if a change is measured between the signal of the reference and the signal obtained by measuring the object to be measured, a determination of whether the change is due to the presence or absence of the object to be measured or whether the change is due to the change in the power of the light source is considered to be difficult.

An objective of an aspect of the present invention is to provide a total reflection spectroscopic measurement device and a total reflection spectroscopic measurement method capable of acquiring information about an optical constant without being affected by a change in power of a light source that generates a terahertz wave.

According to an aspect, there is provided a total reflection spectroscopic measurement device including: a terahertz wave generation unit configured to generate a terahertz wave; an internal total reflection prism having an incident surface and an exit surface for the terahertz wave and configured to exit the terahertz wave from the exit surface by internally propagating the terahertz wave incident from the incident surface and totally reflecting the terahertz wave on a total reflection surface; a detection unit configured to detect the terahertz wave exited from the exit surface of the internal total reflection prism; an electric field vector measurement unit configured to measure an electric field vector of the terahertz wave detected by the detection unit; and an analysis unit configured to acquire information about an optical constant of an object to be measured arranged on the total reflection surface of the internal total reflection prism on the basis of the electric field vector measured by the electric field vector measurement unit, wherein the terahertz wave generated by the terahertz wave generation unit includes S and P polarization components having constant proportions with respect to the total reflection surface; and wherein the analysis unit acquires the information about the optical constant on the basis of a ratio between S and P polarization components of the measured electric field vector when the object to be measured is not arranged on the total reflection surface and a ratio between S and P polarization components of the measured electric field vector when the object to be measured is arranged on the total reflection surface.

Also, according to an aspect, there is provided a total reflection spectroscopic measurement method of acquiring information about an optical constant of an object to be measured on the basis of a terahertz wave totally reflected on a total reflection surface through an inside of an internal total reflection prism having the total reflection surface on which the object to be measured is arranged, the total reflection spectroscopic measurement method including the processes of: causing the terahertz wave including S and P polarization components having constant proportions with respect to the total reflection surface to be incident on the internal total reflection prism when the object to be measured is not arranged on the total reflection surface and measuring an electric field vector of the terahertz wave exited from the internal total reflection prism; causing the terahertz wave to be incident on the internal total reflection prism when the object to be measured is arranged on the total reflection surface and measuring an electric field vector of the terahertz wave exited from the internal total reflection prism; and acquiring the information about the optical constant on the basis of a ratio between S and P polarization components of the measured electric field vector when the object to be measured is not arranged on the total reflection surface and a ratio between S and P polarization components of the measured electric field vector when the object to be measured is arranged on the total reflection surface.

In the total reflection spectroscopic measurement device and the total reflection spectroscopic measurement method as described above, the optical constant is derived on the basis of a ratio between S and P polarization components of an electric field vector measured as a reference when the object to be measured is not arranged and a ratio between P and S polarization components of the measured electric field vector when the object to be measured is arranged. Here, a change in power of a terahertz wave can occur with the passage of time and proportions of the P and S polarization components of the terahertz wave are constant and do not change. Thus, a ratio between the S and P polarization components of the electric field vector measured as the reference is constant regardless of power of the terahertz wave. Therefore, it is possible to derive an optical constant without being affected by a change in power of the light source even when a time interval between measurement of the reference and measurement of the object to be measured is long.

Also, in an aspect, the terahertz wave incident on the internal total reflection prism may be linearly polarized light or circularly polarized light in which the S and P polarization components have the same proportion. According to this configuration, it is possible to perform stable measurement because the S and P polarization components can be radiated without deviation.

Also, in an aspect, the terahertz wave incident on the internal total reflection prism may be linearly polarized light or elliptically polarized light in which proportions of the S and P polarization components are different. According to this configuration, it is not necessary to perform strict alignment so that the proportions of the S and P polarization components are the same.

According to the total reflection spectroscopic measurement device and the total reflection spectroscopic measurement method of the aspects, it is possible to acquire information about an optical constant without being affected by a change in power of a light source that generates a terahertz wave.

DETAILED DESCRIPTION

Hereinafter, an embodiment according to an aspect of the present invention will be specifically described with reference to the drawings. For the sake of convenience, substantially the same elements are denoted by the same reference signs and description thereof may be omitted.

Figure 1:
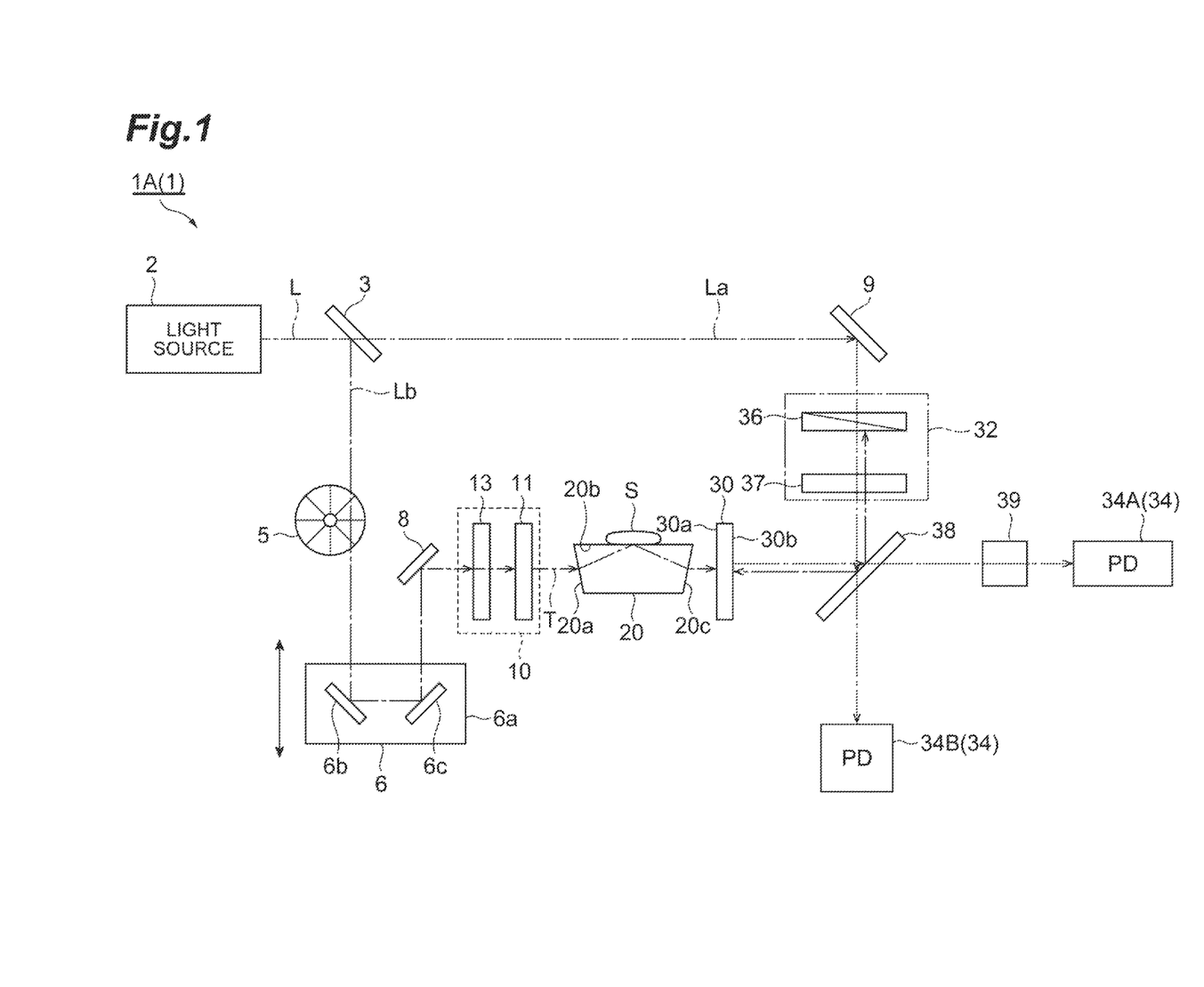
FIG. 1 is a configuration diagram illustrating an optical system of a total reflection spectroscopic measurement device according to an embodiment.

FIG. 1 is a diagram illustrating an optical system of a total reflection spectroscopic measurement device according to the present embodiment. As illustrated in FIG. 1, an optical system 1A of a total reflection spectroscopic measurement device 1 has a terahertz wave generation unit 10 that generates a terahertz wave T using a femtosecond laser as a light source, an internal total reflection prism 20 that totally reflects and exits the terahertz wave T with a total reflection surface 20b, and a terahertz wave detection element (detection unit) 30 that detects the terahertz wave T exited from the internal total reflection prism 20.

More specifically, the optical system 1A of the total reflection spectroscopic measurement device 1 is configured to include a light source 2 that emits a femtosecond laser as outgoing light L, a beam splitter 3 that branches the outgoing light L from the light source 2 into probe light La and pump light Lb, a light modulator 5 that periodically modulates the pump light Lb, a delay stage 6 that temporally delays the pump light Lb with respect to the probe light La, the terahertz wave generation unit 10 that generates a terahertz wave according to incidence of the pump light Lb, the internal total reflection prism 20 having an incident surface 20a, the total reflection surface 20b, and an exit surface 20c for a terahertz wave T, the terahertz wave detection element 30 that detects the terahertz wave T, a polarization adjustment unit 32 that adjusts polarization of the probe light La, and a photodetector 34 that detects the probe light La.

The femtosecond laser emitted from the light source 2 has, for example, a wavelength of 800 nm, a pulse width of 100 fs, a repetitive frequency of 100 MHz, and an average output of 500 mW. The light modulator 5 is, for example, a light chopper, and temporally modulates the pump light Lb with a modulation frequency $f_2$. The modulation frequency $f_2$ is, for example, 1 kHz to 200 kHz. The delay stage 6 has, for example, a stage 6a capable of being reciprocated in the direction of the optical axis of the pump light Lb branched by the beam splitter 3, and a pair of mirrors 6b and 6c for reversing the pump light Lb. The pump light Lb passing through the delay stage 6 is guided to the terahertz wave generation unit 10 by a mirror 8.

The terahertz wave generation unit 10 is a generator for generating a terahertz wave, and includes a terahertz wave generation element 11 and a wave plate 13. The terahertz wave generation element 11 includes, for example, a nonlinear optical crystal such as ZnTe, an antenna element such as an optical switch using GaAs, a semiconductor such as InAs, a superconductor, and the like. Generally, a pulse of the terahertz wave T generated from these elements is about several picoseconds. When the nonlinear optical crystal is used as the terahertz wave generation element 11, the pump light Lb is converted into the terahertz wave T according to a nonlinear optical effect if the pump light Lb is incident on the terahertz wave generation element 11.

The pump light Lb guided to the terahertz wave generation unit 10 by the mirror 8 has its polarization adjusted by the wave plate 13 and is incident on the terahertz wave generation element 11. The terahertz wave T emitted from the terahertz wave generation element 11 is adjusted by the wave plate 13 and the terahertz wave generation element 11 so that the terahertz wave includes the S and P polarization components on the total reflection surface 20b of the internal total reflection prism 20. If a nonlinear optical crystal obtained by cutting out a surface (111) of ZnTe is used as the terahertz wave generation element 11, it is possible to obtain a terahertz wave T including S and P polarization components according to adjustment of the polarization of the pump light Lb by the wave plate 13 and adjustment of the crystal axis of the surface (111) of ZnTe. For example, by making linearly polarized light with an angle of 22.5°, the terahertz wave T becomes linearly polarized light with an angle of 45° on the basis of the total reflection surface 20b with respect to the optical axis. In this case, proportions of the S and P polarization components of the terahertz wave T can be the same. The generated terahertz wave T is incident on the internal total reflection prism 20.

The internal total reflection prism 20 inputs the terahertz wave T output from the terahertz wave generation element 11 to the incident surface 20a, internally propagates the input terahertz wave T, totally reflects the terahertz wave T with the total reflection surface 20b, and outputs the terahertz wave T after the total reflection from the exit surface 20c to the terahertz wave detection element 30. An object S to be measured for various optical constants such as a refractive index, a dielectric constant, and an absorption coefficient is placed on the total reflection surface 20b.

The probe light La is guided to the polarization adjustment unit 32 via a mirror 9. The polarization adjustment unit 32 includes a polarizer 36 and a λ/4 wave plate 37. The probe light La guided to the polarization adjustment unit 32 becomes light linearly polarized by the polarizer 36 in a predetermined direction and further becomes light circularly polarized by the λ/4 wave plate 37.

The circularly polarized probe light La is divided into two while maintaining the polarization state by a non-polarization beam splitter 38. One of the two divisions of the probe light La is guided to the terahertz wave detection element 30, and the other is guided to a second photodetector 34B.

The terahertz wave detection element 30 is a detector for detecting a terahertz wave, and includes an electro-optic crystal obtained by cutting out the surface (111) of ZnTe which is, for example, an optically isotropic medium. One surface 30a of the terahertz wave detection element 30 is an incident surface on which the terahertz wave T is incident. A reflection coating for transmitting the terahertz wave T and reflecting the probe light La is applied to the one surface 30a. Also, the other surface 30b of the terahertz wave detection element 30 is an incident surface on which the probe light La is incident. An antireflection coating for suppressing reflection of the probe light La is applied to the other surface 30b.

Figure 2:
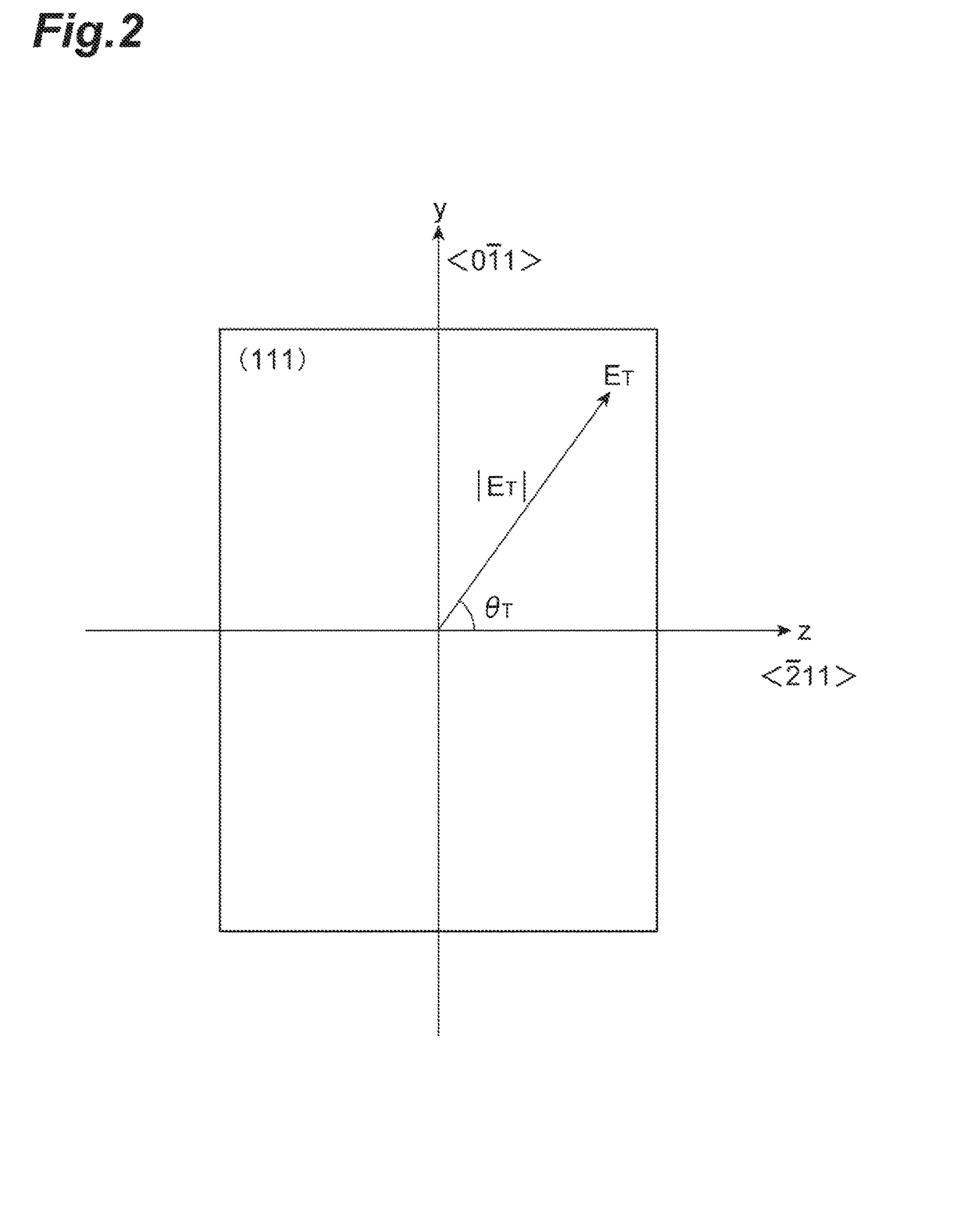
FIG. 2 is a diagram illustrating an electric field vector of a terahertz wave in a terahertz wave detection element.

FIG. 2 is a diagram illustrating the electric field vector of the terahertz wave in the terahertz wave detection element 30. As illustrated in FIG. 2, an electric field vector $E_T$ of the terahertz wave T is represented by an amplitude $|E_T|$ and an azimuth $\theta_T$. At the azimuth $\theta_T$, a direction <−211> in the surface (111) of ZnTe is set to 0°, and the <0−11> direction is set as a positive direction on the basis of the direction <−211>. If a tilt of the electric field of the terahertz wave T with respect to the direction <−211> is 2θ, birefringence is induced in a −θ direction. A magnitude of the birefringence induced in accordance with an intensity of the terahertz wave T is constant regardless of the direction.

The probe light La incident on the terahertz wave detection element 30 is modulated by an electric field of the terahertz wave T at the incident timing and the polarization state changes to elliptical polarization or the like. After the terahertz wave T is probed, the probe light La is reflected by the one surface 30a of the terahertz wave detection element 30 and is incident on the non-polarization beam splitter 38 again. One of two divisions of the probe light La is incident on a rotation analyzer 39 and the other becomes return light.

The rotation analyzer 39 is an element whose analyzer rotates in the surface by a motor or the like. If the probe light La is incident on the analyzer, only specific linearly polarized light is output. Therefore, if the analyzer rotates, the probe light La is modulated. The probe light La modulated by the rotation analyzer 39 is incident on a first photodetector 34A. The return light becomes elliptically polarized light close to linearly polarized light by the λ/4 wave plate 37, and most of the return light is cut by the polarizer 36.

The first photodetector 34A and the second photodetector 34B are, for example, photodiodes. The first photodetector 34A is a photodetector for detecting the probe light La after the terahertz wave T is probed, and detects the probe light La modulated by the rotation analyzer 39. The second photodetector 34B is a photodetector used for monitoring a change in power and detects the probe light La transmitted through the non-polarization beam splitter 38 without going to the terahertz wave detection element 30.

Figure 3:
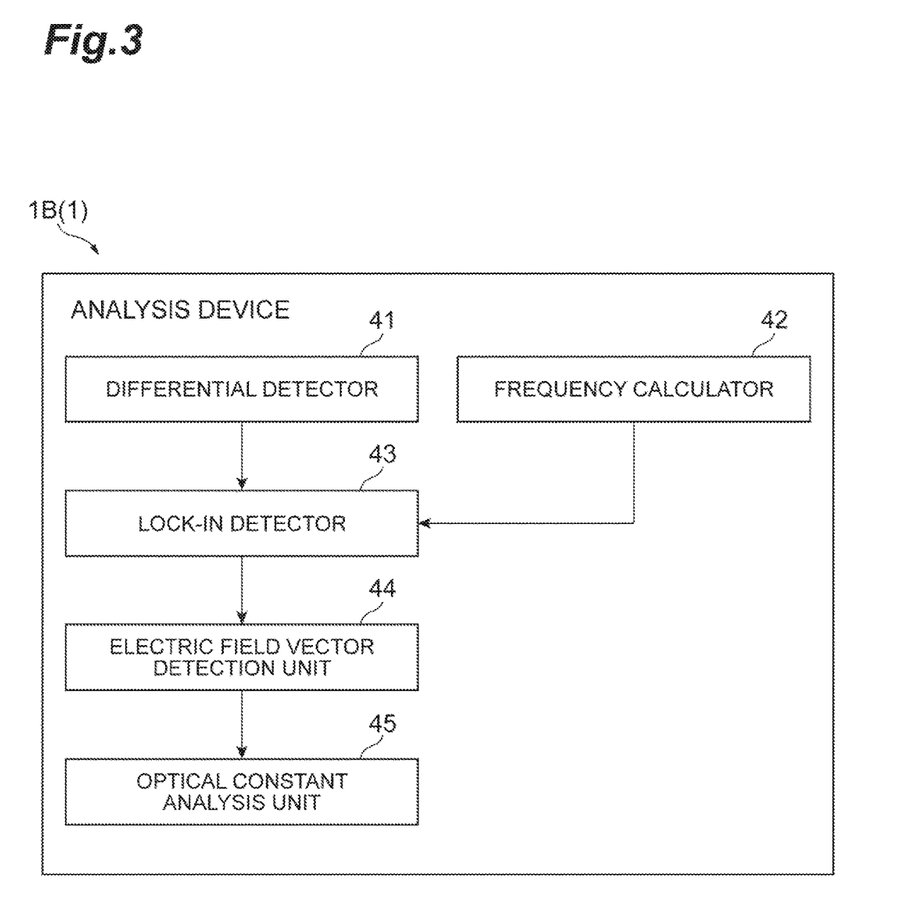
FIG. 3 is a block diagram illustrating a configuration example of an analysis device connected to the optical system of the total reflection spectroscopic measurement device illustrated in FIG. 1.

FIG. 3 is a block diagram illustrating a configuration example of an analysis device 1B connected to the optical system 1A of the above-described total reflection spectroscopic measurement device 1. In the present embodiment, the analysis device 1B which is an analyzer constitutes an electric field vector measurement unit and an analysis unit. As illustrated in FIG. 3, the analysis device 1B includes a differential detector 41, a frequency calculator 42, a lock-in detector 43, an electric field vector detection unit 44, and an optical constant analysis unit 45.

The differential detector 41 is a part that detects a difference between a detection signal from the first photodetector 34A and a detection signal from the second photodetector 34B. The differential detector 41 outputs a detection signal based on the difference between the detection signal from the first photodetector 34A and the detection signal from the second photodetector 34B to the lock-in detector 43. By performing the differential detection, a power change component in the probe light La is eliminated. At this time, it is preferable that sensitivity of the first photodetector 34A and the second photodetector 34B be adjusted so that an intensity of a detection signal of the differential detector 41 becomes zero in a state in which the terahertz wave T is not incident and when the rotation analyzer 39 is not arranged.

The frequency calculator 42 generates a frequency based on a rotation frequency of the rotation analyzer 39 and a modulation frequency of the pump light Lb and outputs a reference signal to the lock-in detector 43. More specifically, the frequency calculator 42 generates a frequency $f_2 \pm 2f_1$ if the rotation frequency of the rotation analyzer 39 is $f_1$ and the modulation frequency of the pump light Lb is $f_2$.

The lock-in detector 43 is a part that detects lock-in of a detection signal from the first photodetector 34A (here, a detection signal from the differential detector 41). The lock-in detector 43 of the present embodiment is a two-phase lock-in detector and simultaneously detects the amplitude and phase of a detection signal that changes in synchronization with the frequency of the reference signal. The lock-in detector 43 performs lock-in detection of the detection signal output from the differential detector 41 using $f_2 \pm 2f_1$ as the frequency of the reference signal. The detection signal from the lock-in detector 43 is output to the electric field vector detection unit 44. The rotation frequency $f_1$ is, for example, 20 Hz to 100 Hz.

The electric field vector detection unit 44 is a part that detects the electric field vector of the terahertz wave T on the basis of the detection signal from the lock-in detector 43. The electric field vector detection unit 44 is physically constituted of a computer system including a CPU, a memory, a communication interface, and the like.

The following relationship is established between an amplitude $A_L$ and a phase $\phi_L$ included in the detection signal from the lock-in detector 43 and an amplitude $|E_T|$ and an azimuth $\theta_T$ of the electric field vector of the terahertz wave T. $A_C$ in the following formula is a constant determined on the basis of a nonlinear optical constant and a thickness of the electro-optic crystal used as the terahertz wave detection element 30, a wavelength of the probe light La, and the like. On the basis of the detection result from the lock-in detector 43, the electric field vector of the terahertz wave T can be uniquely determined by the following formulas.

$$A_L = \frac{1}{2} \sin A_C |E_T| \quad \text{(Formula 1)}$$

$$\phi_L = \frac{\pi}{2} - \theta_T \quad \text{(Formula 2)}$$

If the amplitude of the electric field vector of the terahertz wave T is sufficiently small, the following formula is established. In this case, the amplitude $A_L$ included in the detection signal of the lock-in detector 43 may be set as the amplitude $|E_T|$ of the electric field vector of the terahertz wave T as it is.

$$\sin A_C |E_T| \approx A_C |E_T| \quad \text{(Formula 3)}$$

Also, the two-phase lock-in detector can output each of $A_L \cos \phi_L$ and $A_L \sin \phi_L$ in accordance with the phase of the reference signal. If the amplitude of the electric field vector of the terahertz wave T is sufficiently small, the following formulas are established between these outputs and two axial direction components orthogonal to each other in the electric field vector of the terahertz wave T. Therefore, values $E_{Tx}$ and $E_{Ty}$ proportional to two axial direction components to each other orthogonal in the electric field vector of the terahertz wave T are obtained on the basis of the two outputs output from the lock-in detector 43. In the present embodiment, two axial direction components mutually orthogonal in the electric field vector of the terahertz wave T are made to coincide with S and P polarization components with respect to the total reflection surface of the internal total reflection prism. Thereby, the S and P polarization components of the electric field vector are obtained.

$$E_{Tx} \propto A_L \sin \phi_L \quad \text{(Formula 4)}$$

$$E_{Ty} \propto A_L \cos \phi_L \quad \text{(Formula 5)}$$

The optical constant analysis unit 45 is a part that acquires information about the optical constant of the object to be measured on the basis of the electric field vector measured by the electric field vector detection unit 44. The optical constant analysis unit 45 is physically constituted of a computer system having a CPU, a memory, a communication interface, and the like. The optical constant analysis unit 45 and the electric field vector detection unit 44 may be constituted of the same computer system. For example, the optical constant analysis unit 45 can store data on the S and P polarization components of the measured electric field vector in a memory or the like, and recall the data as necessary.

In the optical constant analysis unit 45 of the present embodiment, information about an optical constant of the object S to be measured is acquired using a ratio $\rho$ between a ratio $R_S$ of the reflectance of the S polarization component and a ratio $R_P$ of the reflectance of the P polarization component in a state in which the object S to be measured is not arranged on the total reflection surface 20b and a state in which the object S is arranged thereon. In this case, the ratio $\rho$ is expressed by the following formula.

$$\rho = \frac{R_P}{R_S} \quad \text{(Formula 6)}$$

Here, if the S and P polarization components of the measured electric field vector when the object S to be measured is not arranged on the total reflection surface 20b are denoted by $E_{S0}$ and $E_{P0}$, respectively, and the S and P polarization components of the measured electric field vector when the object S to be measured is arranged on the total reflection surface 20b are denoted by $E_S$ and $E_P$, respectively, $\rho$ is determined as follows.

$$\rho = \frac{E_P}{E_{P0}} \frac{E_{s0}}{E_s} \quad \text{(Formula 7)}$$

$$\rho = \frac{E_P}{E_s} \frac{E_{s0}}{E_{P0}} \quad \text{(Formula 8)}$$

That is, $\rho$ can be represented by the ratio between the S polarization component $E_{S0}$ and the P polarization component $E_{P0}$ of the measured electric field vector when the object S to be measured is not arranged on the total reflection surface 20b and the ratio between the P polarization component $E_P$ and the S polarization component $E_S$ of the measured electric field vector when the object S to be measured is arranged on the total reflection surface 20b. Using $\rho$ obtained from the S polarization component $E_{S0}$, the P polarization component $E_{P0}$, the P polarization component $E_P$, and the S polarization component $E_S$, the optical constant analysis unit 45 acquires information about optical constants such as a refractive index, a dielectric constant, and an absorption coefficient.

Figure 4:
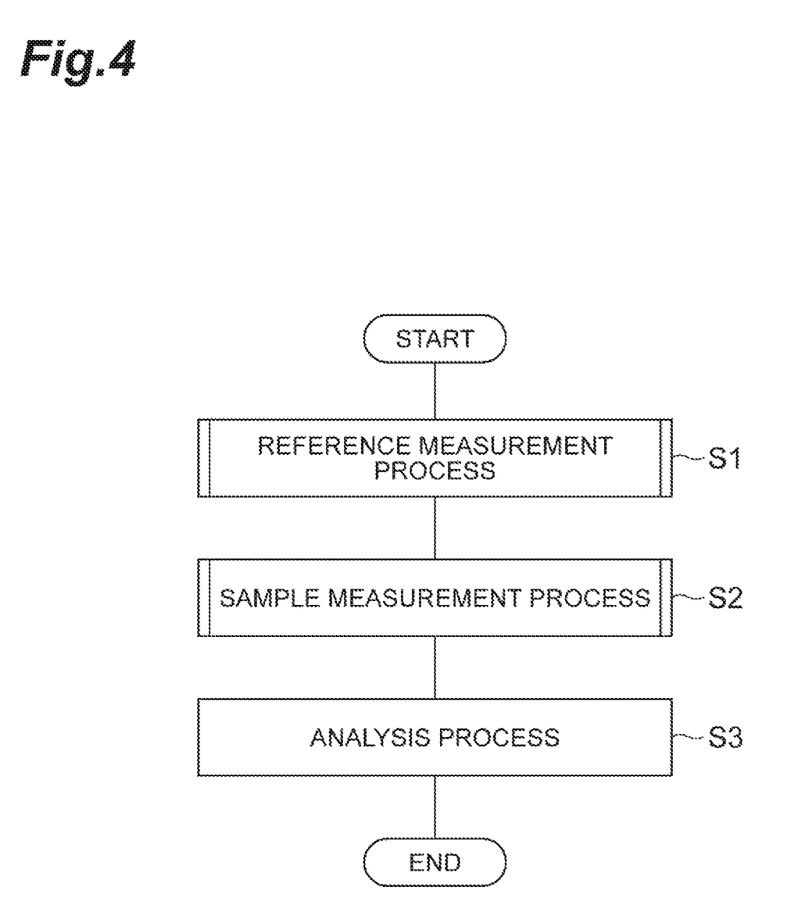
FIG. 4 is a flowchart illustrating a total reflection spectroscopic measurement method according to an embodiment.

FIG. 4 is a flowchart illustrating a total reflection spectroscopic measurement method in the present embodiment. The total reflection spectroscopic measurement method can be executed using the above-described total reflection spectroscopic measurement device 1.

As illustrated in FIG. 4, the total reflection spectroscopic measurement method includes a reference measurement process S1, a sample measurement process S2, and an analysis process S3. In the reference measurement process S1, in a state in which the object S to be measured is not arranged on the total reflection surface 20b, an electric field vector of a terahertz wave T exited from the internal total reflection prism 20 is measured and an S polarization component $E_{S0}$ and a P polarization component $E_{P0}$ are acquired. Also, in the sample measurement process S2, in a state in which the object S to be measured is arranged on the total reflection surface 20b, the electric field vector of the terahertz wave T exited from the internal total reflection prism 20 is measured and an S polarization component $E_S$ and a P polarization component $E_P$ are acquired. The reference measurement process S1 and the sample measurement process S2 are performed under similar environmental conditions.

In the flowchart of FIG. 4, the reference measurement process S1 is performed before the sample measurement process S2, but this order may be reversed. Also, it is not necessary to perform the reference measurement process S1 every time the sample measurement process S2 is performed, and the S polarization component $E_{S0}$ and the P polarization component $E_{P0}$ measured once may be recalled from the memory and used.

Figure 5:
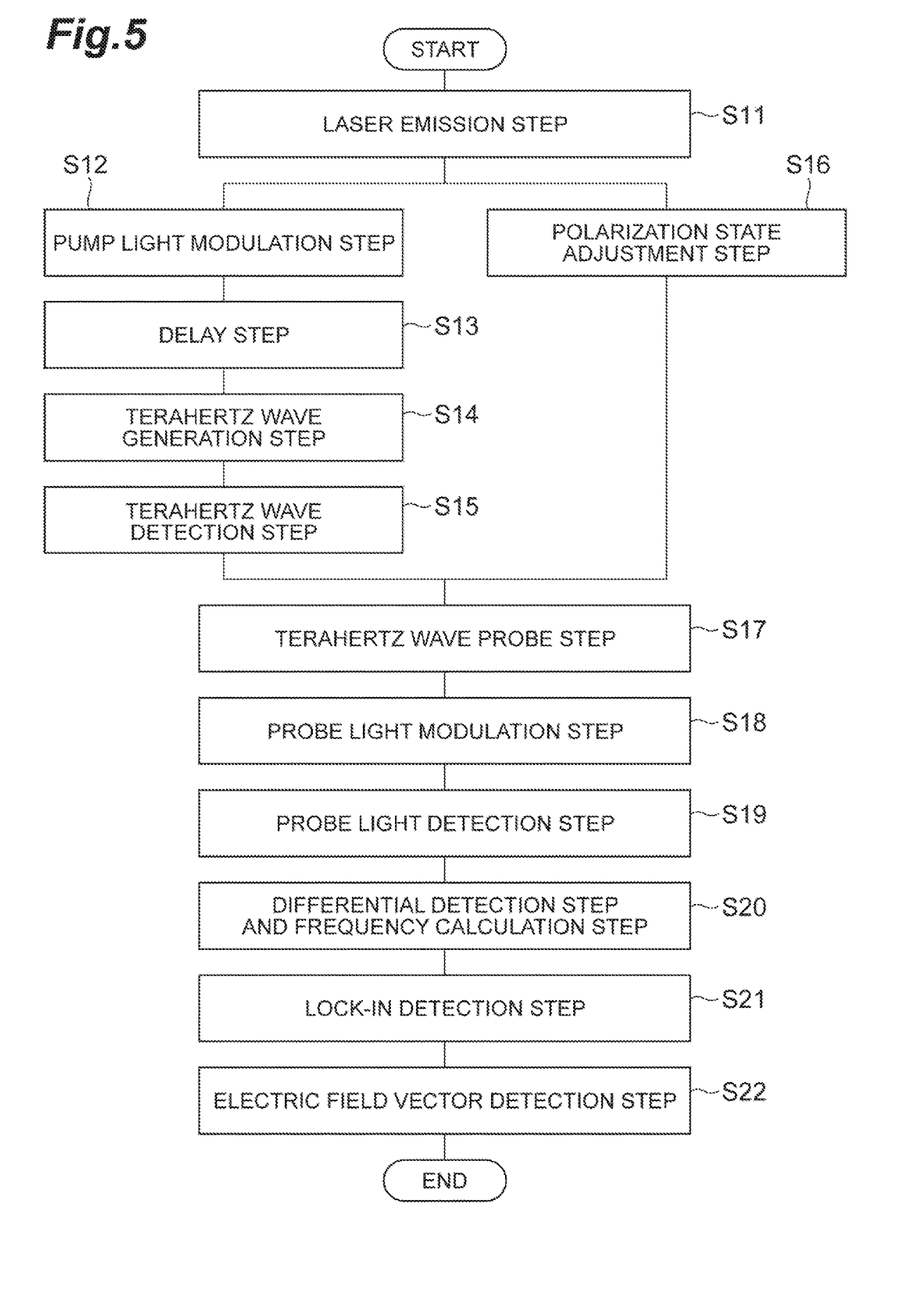
FIG. 5 is a flowchart illustrating an electric field vector detection method.

FIG. 5 is a flowchart illustrating a method of measuring an electric field vector common to the reference measurement process S1 and the sample measurement process S2. As illustrated in FIG. 5, in this method of measuring an electric field vector, the light source 2 first emits outgoing light L which is ultrashort pulse light (step S11: laser emission step). The outgoing light L emitted from the light source 2 is divided into probe light La and pump light Lb by the beam splitter 3. The pump light Lb is temporally modulated by the light modulator 5 (step S12: pump light modulation step), and is temporally delayed by passing through the delay stage 6 (step S13: delay step).

The pump light Lb passing through the delay stage 6 is incident on the terahertz wave generation unit and generates a terahertz wave T (step S14: terahertz wave generation step). The terahertz wave T generated by the terahertz wave generation element 11 is incident on the internal total reflection prism 20, is reflected by the total reflection surface 20b, and is incident on the terahertz wave detection element 30 (step S15: terahertz wave detection step).

On the other hand, the probe light La is guided to the polarization adjustment unit 32 and the polarization state becomes circular polarization (step S16: polarization state adjustment step). Probe light La whose polarization state becomes circular polarization is incident on the terahertz wave detection element 30, and a probe of the terahertz wave T is performed (step S17: terahertz wave probe step). At this time, the polarization state of the terahertz wave T varies according to the electric field vector of the terahertz wave T.

The probe light La after the probe is modulated by the rotation analyzer 39 (step S18: probe light modulation step) and detected by the first photodetector 34A (step S19: probe light detection step). Also, the probe light La unused for the probe is detected by the second photodetector 34B.

Next, detection signals from the first photodetector 34A and the second photodetector 34B are output to the differential detector 41, and differential detection is performed. Also, a frequency based on a rotation frequency of the rotation analyzer 39 and a modulation frequency of the pump light Lb is generated by the frequency calculator 42 and output to the lock-in detector 43 (step S20: differential detection step and frequency calculation step).

When the detection signal from the differential detector 41 is output to the lock-in detector 43, lock-in detection is performed using the frequency generated by the frequency calculator 42 as a reference signal (step S21: lock-in detection step). The detection signal from the lock-in detector 43 is output to the electric field vector detection unit 44, and an amplitude and a direction of the electric field vector of the terahertz wave T are detected on the basis of an amplitude and a phase included in the detection signal from the lock-in detector 43 (step S22: electric field vector detection step).

Returning to FIG. 4 again, in the analysis process S3, ρ is obtained on the basis of the ratio between the S polarization component $E_{S0}$ and the P polarization component $E_{P0}$ of the electric field vector acquired in the reference measurement process S1 and the ratio between the P polarization component $E_{P0}$ and the S polarization component $E_{S0}$ of the electric field vector measured in the sample measurement process S2 and information about the optical constant is acquired. This step is executed by the optical constant analysis unit 45.

Figure 6A:
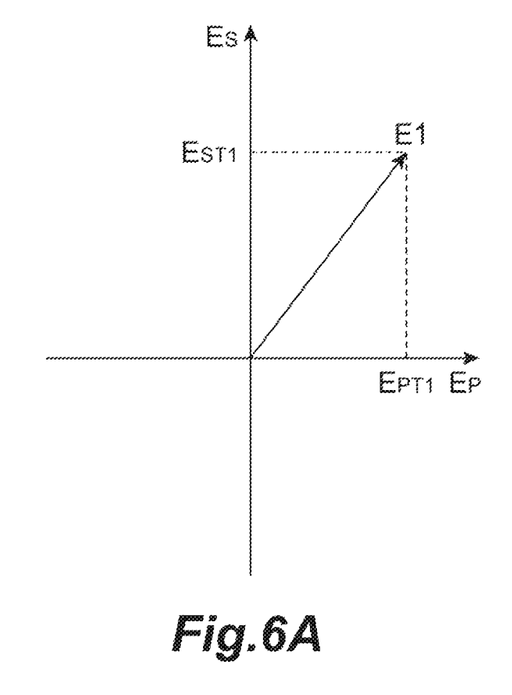
FIG. 6A is a diagram illustrating a relationship between a P polarization component and an S polarization component of a terahertz wave.
Figure 6B:
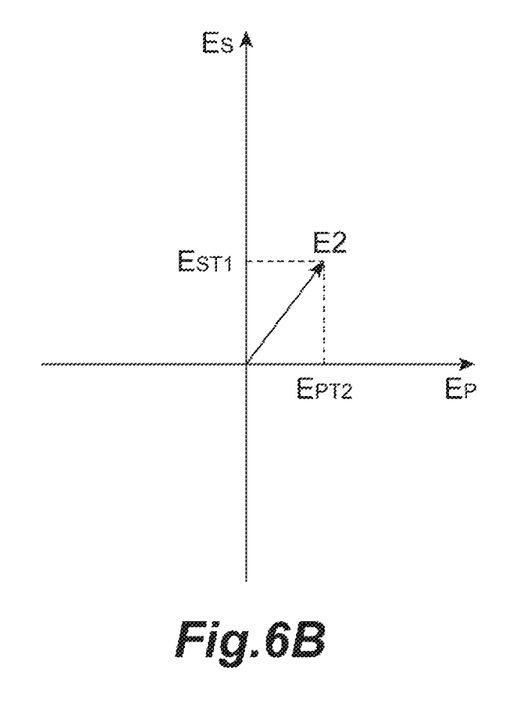
FIG. 6B is a diagram illustrating a relationship between a P polarization component and an S polarization component of a terahertz wave.

Next, the operation and effect of this embodiment will be described. FIGS. 6A and 6B are a diagram schematically illustrating a relationship between the P polarization component and the S polarization component of the terahertz wave generated by the terahertz wave generation unit 10. FIG. 6A illustrates an electric field vector E1 of a terahertz wave generated at a certain timing. FIG. 6B illustrates an electric field vector E2 of a terahertz wave generated at a timing different from that in FIG. 6A. In the illustrated example, power of the terahertz wave in the case of FIG. 6B is less than power of the terahertz wave in the case of FIG. 6A. In this manner, power of two terahertz waves generated in the terahertz wave generation unit 10 at different times may change. Thus, in the conventional technology, even if a change is measured between a signal of a reference and a signal obtained by measuring an object to be measured, a determination of whether the change is due to the presence or absence of the object to be measured or whether the change is due to the change in the power of the light source is considered to be difficult.

In the total reflection spectroscopic measurement device 1 of the present embodiment, an optical constant is derived on the basis of a ratio $E_{S0}/P_{P0}$ of the S polarization component $E_{S0}$ and the P polarization component $E_{P0}$ of the electric field vector measured in the reference measurement process S1 and a ratio $E_P/E_S$ of the P polarization component $E_P$ and the S polarization component $E_S$ of the electric field vector measured in the sample measurement process S2. Here, in the terahertz wave generation unit 10, polarization adjustment of the pump light Lb which is an input femtosecond laser is performed. Thereby, as illustrated in FIGS. 6A and 6B, even when a terahertz wave of different power is generated depending on time, a ratio of an S polarization component $E_{ST1}$ and a P polarization component $E_{PT1}$ of an electric field vector E1 at a certain time is the same as a ratio between an S polarization component $E_{ST2}$ and a P polarization component $E_{PT2}$ of an electric field vector E2 at another time. Thus, the ratio $E_{S0}/E_{P0}$ of the S polarization component $E_{S0}$ and the P polarization component $E_{P0}$ of the electric field vector measured in the reference measurement process S1 is not affected by a change in power of the femtosecond laser. Therefore, even when the power of the femtosecond laser changes with the passage of time between the reference measurement process S1 and the sample measurement process S2, it is possible to derive an optical constant without being affected by a change in the power of the femtosecond laser.

Also, because the terahertz wave T incident on the internal total reflection prism 20 is linearly polarized light in which proportions of the S and P polarization components are the same, it is possible to radiate the S and P polarization components without deviation and perform stable measurement. The terahertz wave T incident on the internal total reflection prism 20 may be circularly polarized light in which proportions of the S and P polarization components are the same.

Although the embodiment has been described in detail with reference to the drawings, the specific configuration is not limited to this embodiment. Measurement of the electric field vector of the terahertz wave exited from the exit surface 20c of the internal total reflection prism 20 can be executed in measurement methods other than the above-described measurement method. For example, an electro-optic crystal obtained by cutting out a surface (111) of ZnTe which is an optically isotropic medium is exemplified as the terahertz wave detection element 30, but an electro-optic crystal may be a crystal obtained by cutting out a surface (111) of another optically isotropic medium such as GaP.

Also, the terahertz wave incident on the internal total reflection prism may be linearly polarized light or elliptically polarized light in which proportions of the S and P polarization components are different. According to this configuration, it is not necessary to perform strict alignment so that the proportions of the S and P polarization components are the same.

What is claimed is:

1. A total reflection spectroscopic measurement device comprising:
    a terahertz wave generation unit configured to generate a terahertz wave;
    an internal total reflection prism having an incident surface and an exit surface for the terahertz wave and configured to exit the terahertz wave from the exit surface by internally propagating the terahertz wave incident from the incident surface and totally reflecting the terahertz wave on a total reflection surface;
    a detection unit configured to detect the terahertz wave exited from the exit surface of the internal total reflection prism;
    an electric field vector measurement unit configured to measure an electric field vector of the terahertz wave detected by the detection unit; and
    an analysis unit configured to acquire information about an optical constant of an object to be measured arranged on the total reflection surface of the internal total reflection prism on the basis of the electric field vector measured by the electric field vector measurement unit, wherein the terahertz wave generated by the terahertz wave generation unit includes S and P polarization components having constant proportions with respect to the total reflection surface;

wherein the analysis unit acquires the information about the optical constant on the basis of a ratio between S and P polarization components of the measured electric field vector when the object to be measured is not arranged on the total reflection surface and a ratio between S and P polarization components of the measured electric field vector when the object to be measured is arranged on the total reflection surface; and wherein the ratio between the S-polarization component and the P-polarization component of the electric field vector, when the object to be measured is not arranged on the total reflection surface, are measured before the ratio between S and P polarization components when the object to be measured is arranged on the total reflection surface.

2. The total reflection spectroscopic measurement device according to claim 1, wherein the terahertz wave generated by the terahertz wave generation unit is linearly polarized light or circularly polarized light in which proportions of the S and P polarization components are the same.

3. The total reflection spectroscopic measurement device according to claim 1, wherein the terahertz wave generated by the terahertz wave generation unit is linearly polarized light or elliptically polarized light in which proportions of the S and P polarization components are different.

4. A total reflection spectroscopic measurement method of acquiring information about an optical constant of an object to be measured on the basis of a terahertz wave totally reflected on a total reflection surface through an inside of an internal total reflection prism having the total reflection surface on which the object to be measured is arranged, the total reflection spectroscopic measurement method comprising the processes of:

causing the terahertz wave including S and P polarization components having constant proportions with respect to the total reflection surface to be incident on the internal total reflection prism when the object to be measured is not arranged on the total reflection surface and measuring an electric field vector of the terahertz wave exited from the internal total reflection prism;

causing the terahertz wave including S and P polarization components with respect to the total reflection surface at the proportions to be incident on the internal total reflection prism when the object to be measured is arranged on the total reflection surface and measuring an electric field vector of the terahertz wave exited from the internal total reflection prism; and acquiring the information about the optical constant on the basis of a ratio between S and P polarization components of the measured electric field vector when the object to be measured is not arranged on the total reflection surface and a ratio between S and P polarization components of the measured electric field vector when the object to be measured is arranged on the total reflection surface, wherein the ratio between the S-polarization component and the P-polarization component of the electric field vector, when the object to be measured is not arranged on the total reflection surface, are measured before the ratio between S and P polarization components when the object to be measured is arranged on the total reflection surface.

5. The total reflection spectroscopic measurement method according to claim 4, wherein the terahertz wave incident on the internal total reflection prism is linearly polarized light or circularly polarized light in which proportions of the S and P polarization components are the same.

6. The total reflection spectroscopic measurement method according to claim 4, wherein the terahertz wave incident on the internal total reflection prism is linearly polarized light or elliptically polarized light in which proportions of the S and P polarization components are different.

* * * * *